(12) United States Patent
Uchiyama et al.

(10) Patent No.: US 7,498,145 B2
(45) Date of Patent: Mar. 3, 2009

(54) CONCENTRATION MEASURING METHOD, CONCENTRATION MEASURING KIT, AND SENSOR CHIP FOR USE IN THE METHOD

(75) Inventors: Kenichi Uchiyama, Chigasaki (JP); Kayoko Oomiya, Yokohama (JP); Isao Kishimoto, Yokohama (JP); Masami Hirata, Yokkaichi (JP); Hideo Eto, Yokohama (JP); Ichiro Tono, Yokohama (JP); Ikuo Uematsu, Yokohama (JP); Shingo Kasai, Yokohama (JP); Tomohiro Takase, Sagamihara (JP); Tsutomu Honjoh, Yokohama (JP); Masanori Sugitani, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 163 days.

(21) Appl. No.: 11/363,094

(22) Filed: Feb. 28, 2006

(65) Prior Publication Data
US 2006/0194345 A1      Aug. 31, 2006

Related U.S. Application Data

(63) Continuation of application No. PCT/JP2004/012393, filed on Aug. 27, 2004.

(30) Foreign Application Priority Data
Aug. 29, 2003   (JP)   ............... 2003-307920

(51) Int. Cl.
*G01N 33/53* (2006.01)
*G01N 33/551* (2006.01)
*G01N 33/552* (2006.01)
*G01N 33/58* (2006.01)

(52) U.S. Cl. ............. 435/7.92; 385/12; 385/129; 385/130; 422/58; 422/82.11; 435/288.4; 435/288.7; 435/808; 436/164; 436/172; 436/518; 436/524; 436/525; 436/527; 436/805

(58) Field of Classification Search ............... None
See application file for complete search history.

(56) References Cited

U.S. PATENT DOCUMENTS 3,867,518 A * 2/1975 Coffey et al. ............... 436/539

(Continued)

FOREIGN PATENT DOCUMENTS

EP       1 174 522 A2     1/2002

(Continued)

OTHER PUBLICATIONS

U.S. Appl. No. 11/566,857, filed Dec. 5, 2006, Uematsu et al.
U.S. Appl. No. 11/363,094, filed Feb. 28, 2006, Uchiyama et al.

*Primary Examiner*—Christopher L Chin
(74) *Attorney, Agent, or Firm*—Oblon, Spivak, McClelland, Maier & Neustadt, P.C.

(57) ABSTRACT

The method for measuring the concentration of the measuring object uses a sensor chip comprising an optical waveguide layer and an antibody immobilized layer formed on the surface of the optical waveguide layer, which comprises immobilizing the measuring object and an enzyme-labeled antibody labeled with a labeling enzyme on the antibody immobilized layer of the sensor chip having an immobilized antibody, producing a color-developing and precipitating enzyme reaction product by allowing to react a coloring reagent with the labeling enzyme on the antibody immobilized layer to precipitate the enzyme reaction product on the antibody immobilized layer, allowing to totally reflect a light impinged on the sensor chip from the outside at an interface between the optical waveguide layer and the antibody immobilized layer, and observing to a physical value of the totally reflected light.

16 Claims, 13 Drawing Sheets

U.S. PATENT DOCUMENTS

| | | | |
|---|---|---|---|
| 4,444,879 A * | 4/1984 | Foster et al. | 435/7.95 |
| 4,608,344 A | 8/1986 | Carter et al. | |
| 6,312,961 B1 | 11/2001 | Voirin et al. | |
| 6,429,022 B1 | 8/2002 | Kunz et al. | |
| 2003/0203395 A1 | 10/2003 | Begovich et al. | |
| 2005/0084909 A1 | 4/2005 | Uchiyama et al. | |
| 2006/0194345 A1 | 8/2006 | Uchiyama et al. | |

FOREIGN PATENT DOCUMENTS

| | | | |
|---|---|---|---|
| JP | 3-007270 | | 2/1991 |
| JP | 8-285851 | | 11/1996 |
| JP | 2002-330755 | | 11/2002 |
| JP | 2003-240704 | | 8/2003 |
| JP | 2003-329684 | | 11/2003 |
| WO | 90/11525 | * | 10/1990 |
| WO | WO 91/06672 | | 5/1991 |

* cited by examiner

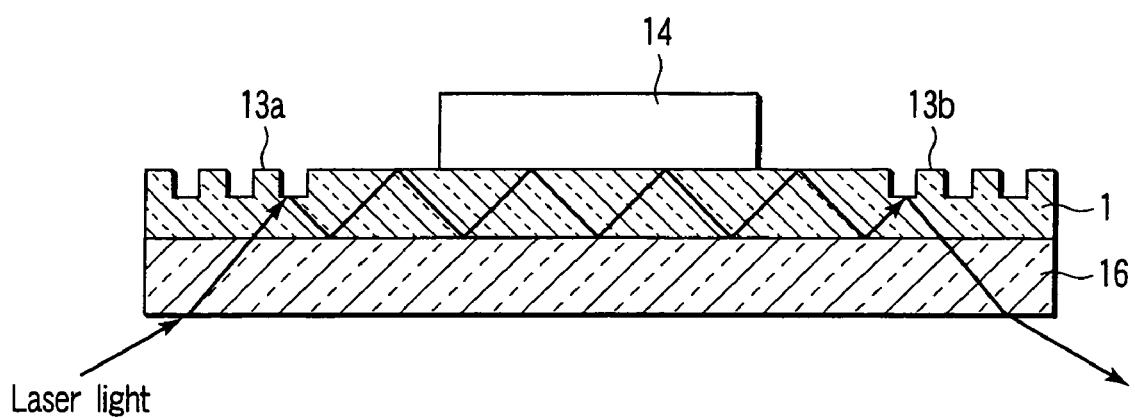
F I G. 1

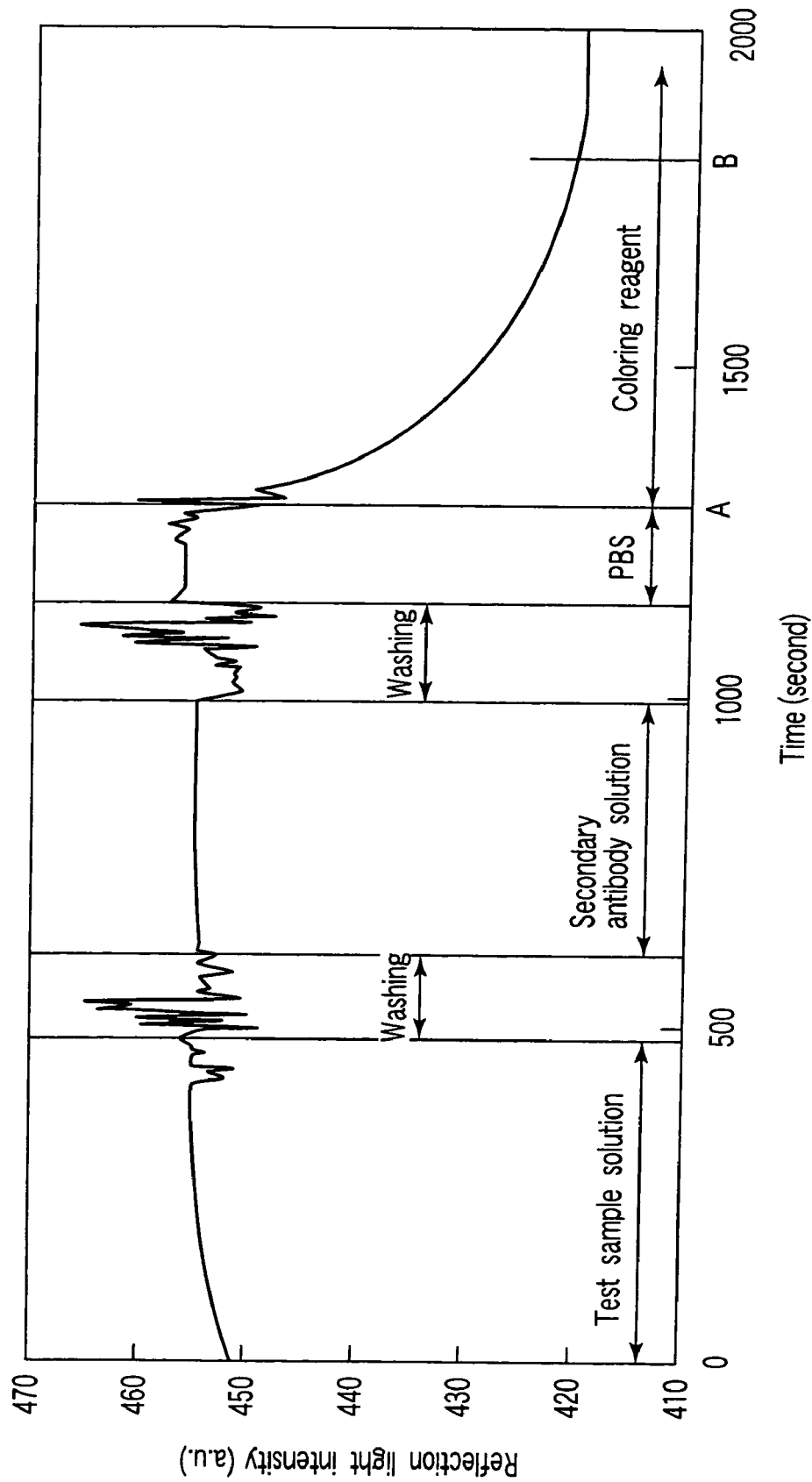
F I G. 8

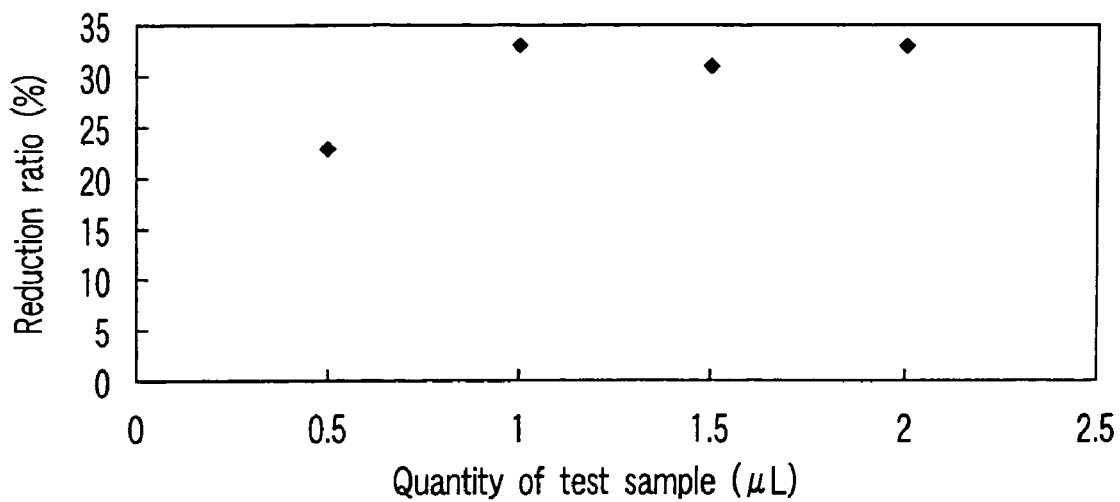
F I G. 9
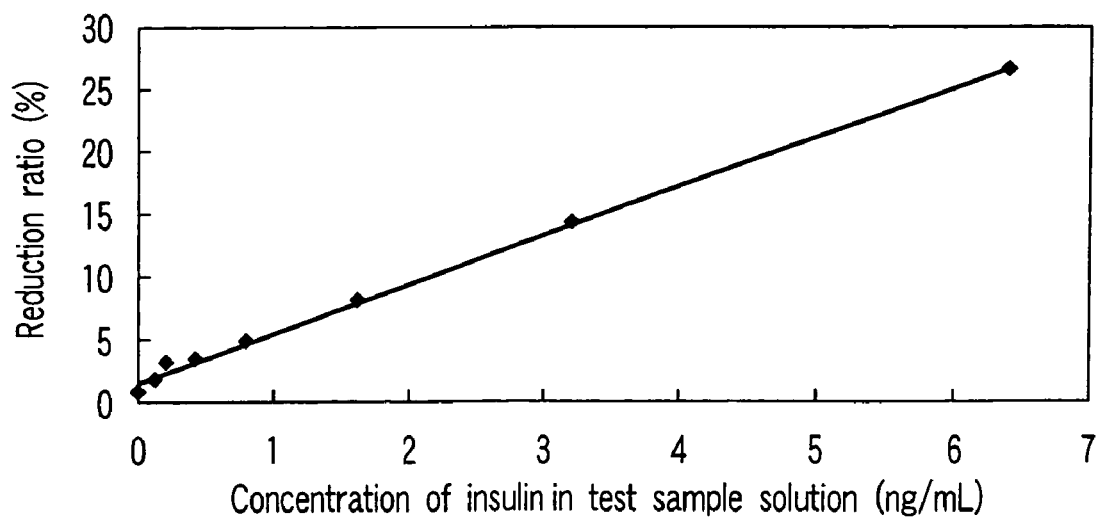
F I G. 10

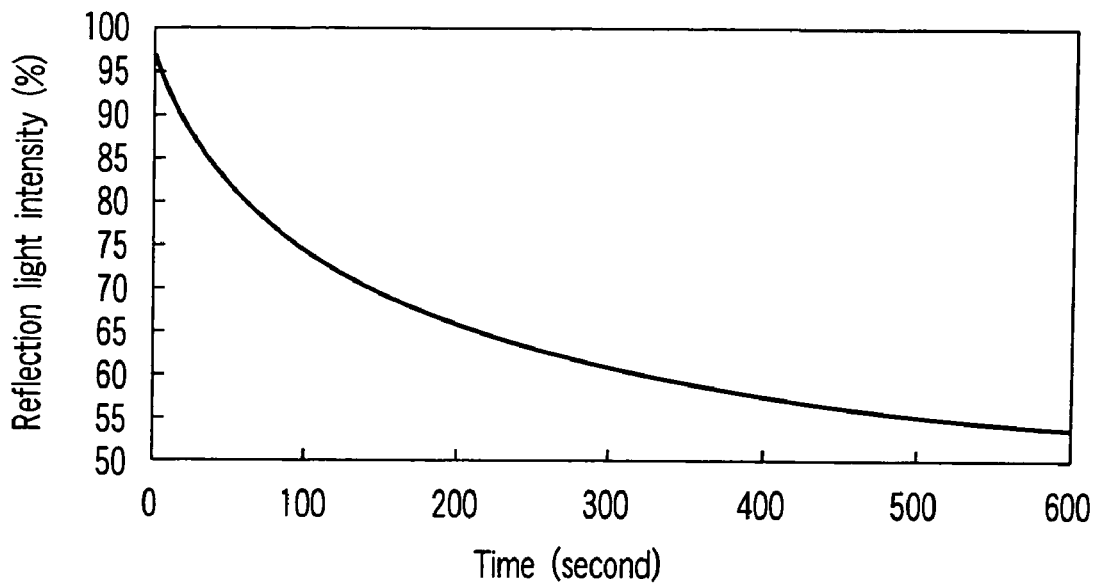
F I G. 13
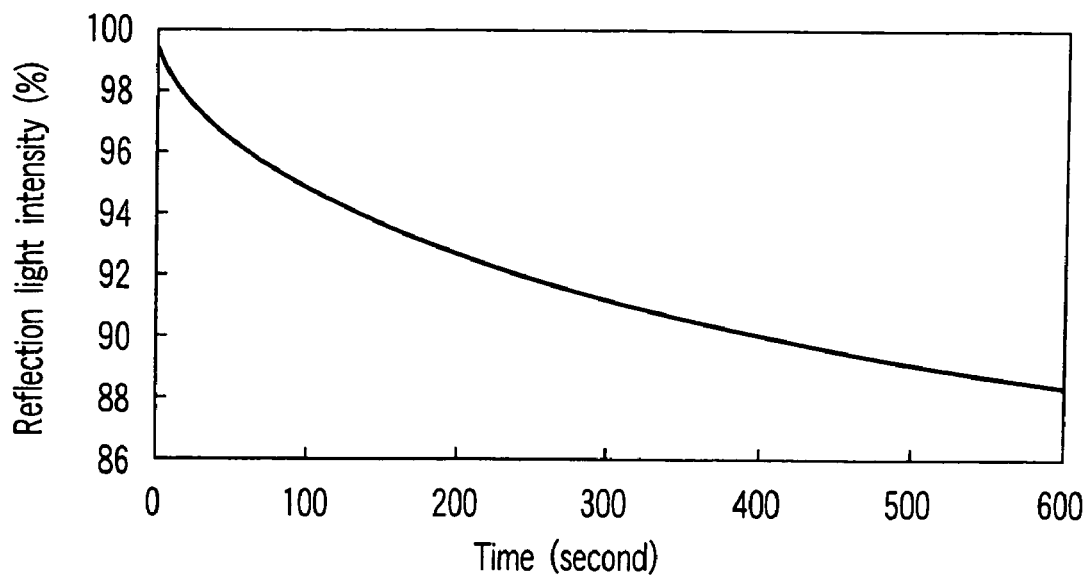
F I G. 14

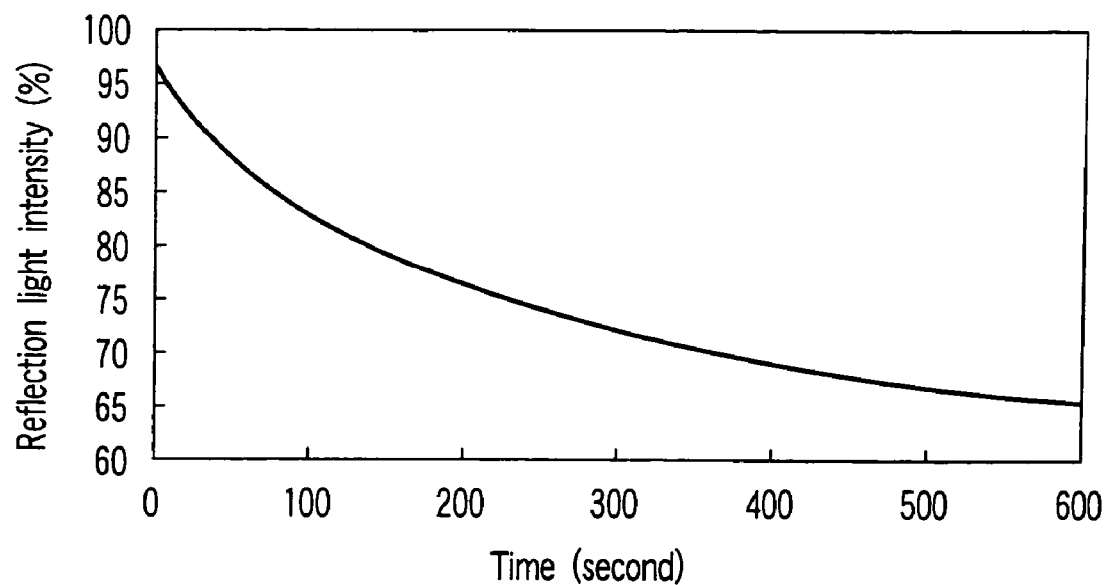
F I G. 15
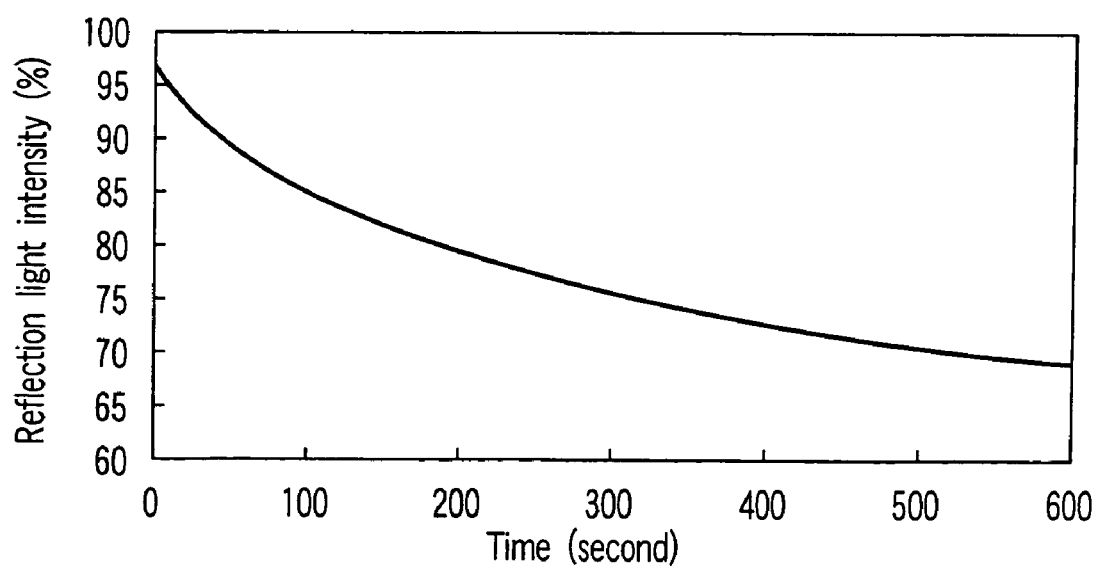
F I G. 16

CONCENTRATION MEASURING METHOD, CONCENTRATION MEASURING KIT, AND SENSOR CHIP FOR USE IN THE METHOD

CROSS REFERENCE TO RELATED APPLICATIONS

This is a Continuation Application of PCT Application No. PCT/JP2004/012393, filed Aug. 27, 2004, which was published under PCT Article 21(2) in Japanese.

This application is based upon and claims the benefit of priority from prior Japanese Patent Application No. 2003-307920, filed Aug. 29, 2003, the entire contents of which are incorporated herein by reference.

BACKGROUND OF THE INVENTION

1. Field of the Invention

The invention relates to a method for measuring the concentration of a measuring object, a concentration measuring kit, and a sensor chip for use in the method. Particularly, the invention relates to a coloring reagent employed in an enzyme reaction for rapidly measuring the concentration of a measuring object using a very small quantity of a sample with high sensitivity and high accuracy by taking advantage of an evanescent wave, a concentration measuring kit, a method for measuring the concentration of a measuring object, and a sensor chip for use in the method.

2. Description of the Related Art

An enzyme-linked immunosorbent assay (ELISA) method has been practically used in clinical examinations as a method for measuring a very small quantity of a component by taking advantage of a specific reaction between an antigen and antibody.

A resin plate having 96 pits (wells) usually called as a microplate is used for the ELISA method. For example, a primary antibody is immobilized on each well depending on the object of assay in a sandwich ELISA method. In this method, a test sample solution is dispensed in each well, and the antibody (primary antibody) immobilized on the plate is allowed to react with a measuring object in the test sample solution (referred to a primary reaction hereinafter) followed by removing a solution containing the unreacted test sample by washing. Then, a solution of a secondary antibody labeled with an enzyme is dispensed in each well of the plate to permit the measuring object reacted with the secondary antibody to specifically react with the measuring object (referred to a secondary reaction hereinafter). After removing the solution of the unreacted secondary antibody, a solution of a coloring reagent is dispensed in each well for permitting an enzyme reaction to proceed (referred to an enzyme reaction hereinafter) to allow the enzyme reaction product to develop a color, and the concentration of the measuring object is determined from a calibration curve by measuring absorbance from the intensity of transmitted light through the well using a microplate reader.

For example, insulin is a hormone secreted from β-cells of the pancreas, and is known to have an action for decreasing the blood glucose level. Accordingly, the concentration of insulin in the blood should be measured for diagnosis of diabetes and for recognizing the pathology of the patient. The insulin concentration is measured by the same method as described above by ELISA using a microplate having wells in which an anti-insulin antibody is immobilized by dispensing a test sample solution in this well to allow the anti-insulin antibody to react with insulin in the test sample solution.

However, an amount of the test sample of several tens of microliters to 100 microliters is required for ELISA using the microplate, or 5 μL or more at the smallest, and sensitivity of the measurement reduces in the order of only about several hundreds of picograms per mL at a concentration described above. In addition, the reaction system is affected by an increased amount of inhibitory substances for the antigen-antibody reaction involved in the test sample solution when the amount of the test sample subjected to the measurement is increased in order to enhance sensitivity. Since sensitivity of the measurement may be rather decreased by increasing the amount of the test sample, it remains to be only about several hundreds of picograms per mL.

It is another problem of ELISA that the measurement takes a long time since the reaction time becomes long before the antigen-antibody reaction is completed in ELISA which requires a large amount of the test sample. For example, the time required for the primary reaction is usually several hours, or 24 hours at the longest, and the secondary reaction and substrate reaction require several tens minutes.

The amount of the test sample (blood, plasma) is desirably as small as possible when the test sample is collected from an infant or a small animal. While the amount of the test sample dispensed in the wells of the microplate is required to be accurate in ELISA, it is difficult to accurately measure an amount as small as less than 5 μL. Accordingly, the test sample in an amount of more than necessary should be sampled for accurate measurements, although it is desirable to subject a smaller amount of the sample to the measurement.

A sensor chip taking advantage of the antigen-antibody reaction has been known. FIG. 1 is a schematic illustration showing the construction of a sensor chip having an optical waveguide. The sensor chip comprises an optical waveguide layer 1 made of a silicon nitride film formed on a glass base plate 16, a pair of an incident side grating (diffraction grating) 13a and outgoing side grating 13b, or prisms (not shown), disposed at both sides of the optical waveguide layer, respectively, and an antibody immobilized layer 14 formed on the optical waveguide layer 1.

An antigen-antibody reaction occurs by allowing a test sample solution containing an antigen to contact the antibody immobilized layer 14 in such a sensor chip. An immune complex comprising antibody/antigen/fluorescent pigment-labeled antibody is formed on the base plate by adding a fluorescent pigment-labeled antibody solution in the antigen-antibody reaction system. The amount of the antigen in the test sample solution is assayed by the steps comprising: allowing a laser light to impinge through the incident side grating 13a into the optical waveguide layer 1 to emit an evanescent wave; exciting the fluorescent pigment by the evanescent wave in the antibody immobilized layer 14 on the optical waveguide layer 1; and analyzing the amount of the antigen in the test sample solution by detecting the intensity of fluorescence emitted from the fluorescent pigment with a photo-acceptance element (see, for example, Japanese Patent Application Laid-Open (JP-A) No. 8-285851).

The evanescent wave refers to an electromagnetic wave localizing at near an interface where a light is totally reflected at the interface between the optical waveguide layer and an external layer. Known measuring methods using the evanescent wave include a method for detecting a change in a physical value of the reflection light due to absorption of the evanescent wave in a pigment-labeled substance (for example a pigment-labeled secondary antibody) in the test sample, in addition to the method for labeling the test sample with the fluorescent pigment (see, for example, Jpn. Pat. Appln. KOKOKU Publication No. 3-7270).

In these conventional measuring methods, however, the number of the pigments or fluorescent pigments incorporated into the immune complex becomes small to make the measurement difficult when the concentration of the measuring object in the test sample is low. Accordingly, the photo-acceptance element for detecting the changes of the physical value of the reflection light should be highly sensitive to render the element to be expensive while the apparatus for detecting the changes of the physical value of the reflection light also becomes complicated and expansive.

BRIEF SUMMARY OF THE INVENTION

An object of the invention performed with reference to the present situations described above is to provide, for measuring the concentration of a measuring object, a kit for measuring the concentration, and a sensor chip for use in the method, wherein the concentration of the measuring object in a test sample solution with a quite small volume of 5 µL or less can be measured in a short period of time, and is able to be promptly measured with high accuracy even when the amount of the test sample is inaccurate.

The inventors of the invention have found, through intensive studies, that the above-mentioned object can be attained by using a coloring reagent that forms precipitates of an enzyme reaction product when a color is developed by the enzyme reaction in the method for measuring the density by taking advantage of the enzyme reaction, and by measuring a change of a physical value of a light ascribed to the precipitated enzyme reaction product.

According to first aspect of the present invention, there is provided a method for measuring the concentration of a measuring object using a sensor chip having an optical waveguide layer and an antibody immobilized layer provided on the surface of the optical waveguide layer, which comprises:

immobilizing the measuring object and an enzyme-labeled antibody labeled with a labeling enzyme on the antibody immobilized layer of the sensor chip having an immobilized antibody;

producing a color-developed enzyme reaction product by allowing to react a coloring reagent with the labeling enzyme on the antibody immobilized layer, precipitating the enzyme reaction product on the antibody immobilized layer;

allowing to totally reflect a light impinged on the sensor chip from the outside at an interface between the optical waveguide layer and the antibody immobilized layer; and observing to a physical value of the totally reflected light.

According to second aspect of the present invention, there is provided a method for measuring the concentration of a measuring object using a sensor chip having an optical waveguide layer and an antibody immobilized layer provided on the surface of the optical waveguide layer, which comprises:

immobilizing the measuring object and an enzyme-labeled antibody labeled with a labeling enzyme with the antibody immobilized layer of the sensor chip having an immobilized antibody, and allowing to totally reflect a light impinged on the sensor chip from the outside at an interface between the optical waveguide layer and the antibody immobilized layer to observe a physical value of the total reflection light; and producing a color-developed enzyme reaction product by allowing a coloring reagent to react with the labeling enzyme, precipitating the enzyme reaction product on the antibody immobilized layer, and allowing to totally reflect a light impinged on the sensor chip from the outside at an interface between the optical waveguide layer and the antibody immobilized layer to observe a physical value of the total reflection light.

According to third aspect of the present invention, there is provided a kit for measuring the concentration of a measuring object, which comprises:

an antibody labeled with a labeling enzyme;

a coloring reagent containing at least a coloring substrate and a substrate for the labeling enzyme, the coloring reagent developing a color by an enzyme reaction and forming a precipitating enzyme reaction product; and a sensor chip having am antigen immobilized layer formed on the surface of an optical waveguide layer including a region for totally reflecting a light introduced into the region, wherein the sensor chip, the antibody and the coloring reagent are independently packed and assembled together.

According to fourth aspect of the present invention, there is provided a sensor chip comprising:

an optical waveguide layer configured to propagate a light within the layer by total reflection of the light;

an antibody immobilized layer formed at least a part of the surface of the optical waveguide layer for total reflection of the light;

a frame member adhered on the surface of the optical waveguide layer, surrounding the antibody immobilized layer, for constituting a cell; and a liquid-repelling film formed on that part of the optical waveguide layer, other than that part on which at least the frame member is provided, having a surface at a level higher than the antibody immobilized layer and lower than the frame member, and having an reaction hole exposing at least one part of the antibody immobilized layer.

BRIEF DESCRIPTION OF THE SEVERAL VIEWS OF THE DRAWING

FIG. 1 is a schematic drawing showing a construction of a sensor chip.

FIG. 8 is a graph showing the result of measurement by the method according to the invention.

FIG. 9 is a graph of a measurement result showing non-dependency of the measurement of rat insulin on sample volume obtained in Example 1.

FIG. 10 is a graph of a measurement result showing dependency of the measurement of rat insulin on sample volume obtained in Example 1.

FIG. 13 is a graph showing the result of measurement on casein obtained in Example 4.

FIG. 14 is a graph showing the result of measurement on β-lactoglobulin obtained in Example 5.

FIG. 15 is a graph showing the result of measurement on ovoalbumin obtained in Example 6.

FIG. 16 is a graph showing the result of measurement on a major buckwheat protein complex obtained in Example 7.

DETAILED DESCRIPTION OF THE INVENTION

Figure 2:
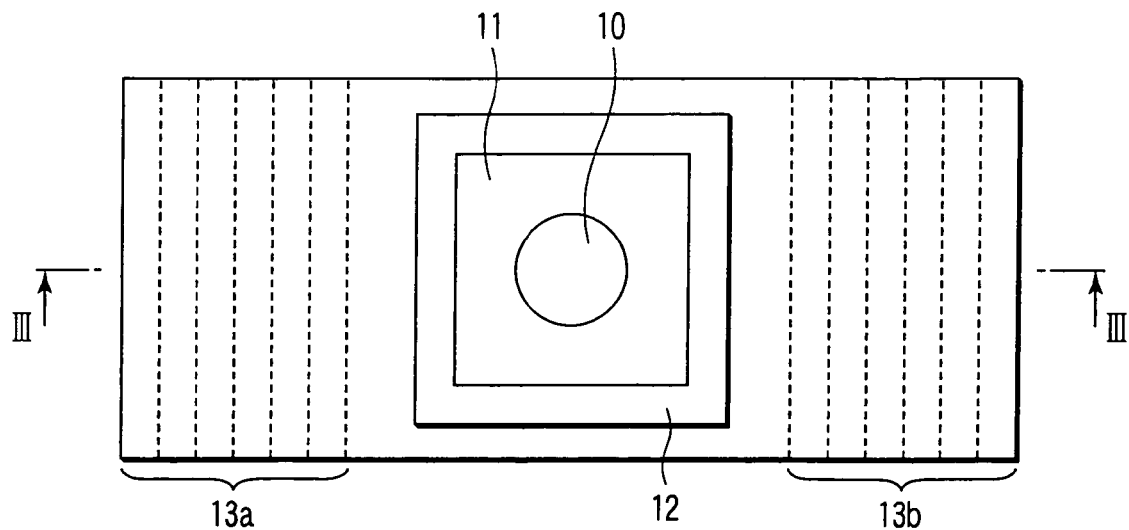
FIG. 2 is a top view of a sensor chip of an example of the sensor chip according to the embodiment of the invention.

Embodiments of the invention are described below in the order of a concentration measuring kit of a measuring object, a coloring reagent and a sensor chip as constituting elements of the concentration measuring kit, and a concentration measuring method using them.

(Concentration Measuring Kit)

The concentration measuring kit for the measuring object of the invention (referred to a concentration measuring kit or simply a kit hereinafter) is constructed so that the coloring reagent develops a color and precipitates by an enzyme reaction.

The concentration measuring kit of the invention comprises a sensor chip providing an antibody immobilized layer for trapping a measuring object on the surface of an optical waveguide, a stock solution of an antibody labeled with an enzyme, and a coloring reagent that contains a coloring substrate and a labeling enzyme, and generates an enzyme reaction product that develops a color and forms precipitates by the enzyme reaction, and these components are independently packed and assembled.

The concentration measuring kit of the invention can be favorably used for sandwich ELISA.

Examples of the measuring object include proteins, peptides and genes contained in blood, serum, plasma, biological specimens and foods. Specific examples of them include, although not restrictive, insulin, casein, β-lactoglobulin, ovoalbumin, calcitonin, C-peptide, leptin, β-2-microgloburin, lethinol-binding protein, α-1-microglobulin, α-fetoprotein, carcinoembryonic antigen, troponin-I, glucagons-like peptide, insulin-like peptide, tumor growth factor, fibroblast growth factor, platelet growth factor, epithelial cell growth factor, hapten hormones such as cortisol, triiode thyronine, thyroxin, drugs such as digoxin and theophylline, infectious substances such as bacteria and viruses, hepatitis antibody and IgE, as well as major protein complex of buckwheat and soluble proteins including Arah2 of peanuts.

The invention may be favorably used for measuring the concentration of proteins with a molecular weight of 5000 or more. In particular, the invention may be favorably applied when the antigen is insulin, particularly insulin from human, mouse, rat or hamster, or a protein contained in foods, particularly casein, β-lactoglobulin, ovoalbumin, a major protein complex of buckwheat and a soluble protein containing Arah2 of peanuts.

The concentration of the measuring object is not particularly restricted, and plasma, serum and whole blood may be directly used.

In the preferred embodiment of the concentration measuring kit of the invention, the kit is provided by packing, in respective vessels, a sensor chip having an antibody immobilized layer for trapping the measuring object on the surface of an optical waveguide, a stock solution of an antibody labeled with an enzyme such as horseradish peroxidase (also containing a carrier protein, surfactant and buffer solution), a coloring reagent in which a coloring substrate (such as benzidine coloring reagent) and a substrate for the labeling enzyme (such as hydrogen peroxide) are mixed, a reference substance for the measuring object, and a buffered physiological saline for washing the base plate.

For example, an insulin measuring kit comprises a set of eight sensor chips having an antibody immobilized layer for trapping the measuring object on the surface of an optical waveguide; a stock solution of an enzyme-labeled anti-insulin antibody; a diluting liquid for the enzyme-labeled anti-insulin antibody (a buffer solution or a solution in which the buffer solution is combined with a surfactant); a coloring reagent solution in which reagents comprising a coloring substrate and a substrate for a labeling enzyme are mixed (a solution containing $H_2O_2$ and TMBZ solutions); a solution for diluting the test sample; a reference insulin (freeze dried); a cleaning solution (such as a solution in which a buffer solution and surfactant are combined, a phosphate-buffered physiological saline (PBS) containing a surfactant, a Tris-buffered saline, and a Good's buffer-buffered physiological saline); and a phosphate buffer. These components are independently packed and assembled. More preferably, cotton cloth, a plate for temporarily placing the sensor chip, a branched micropipette (8-connected pipettes), tweezers and reaction Petri dishes are also assembled in the kit, if necessary. An insulin reference solution is prepared by dissolving freeze-dried reference insulin in purified water.

(Coloring Reagent)

The coloring reagent of the invention contains at least a coloring substrate and a labeling enzyme substrate, which are largely featured in generating an enzyme reaction product that develops a color by an enzyme reaction and is precipitated. The coloring reagent is dissolved in a buffer solution, and is used as a coloring reagent solution comprising a surfactant and an organic solvent when necessary.

The preferable embodiment of the coloring reagent of the invention is a benzidine-base coloring reagent comprising benzidine as a coloring substrate and hydrogen peroxide as a substrate of the labeling enzyme.

Examples of the preferable benzidine-base coloring reagent include 4-chloro-1-naphtol, 3,3'-diaminobenzidine and 3,3',5,5'-tetramethyl benzidine. Preferable among them from the view point of sensitivity of the measurement are 3,3',5,5'-tetramethyl benzidine (abbreviated as TMBZ hereinafter) and a hydrochloride thereof (3,3',5,5'-tetramethyl benzidine.$2HCl.2H_2O$). The benzidine-base coloring reagent of a salt form may be directly added in an aqueous medium, and the coloring reagent of a non-salt form may be added in the aqueous medium after dissolving in a small amount of an organic solvent. The solvent may be diluted to an extent not affecting the performance of the solution. These benzidine coloring reagents may be used alone, or as a combination of at least two of them.

Hydrogen peroxide may be used, for example, a peroxide.

While redox enzymes used for the labeling enzyme are not particularly restricted, examples of them include active enzymes such as peroxidase and catalase extracted from horseradish, cow's milk and white blood cells. Horseradish peroxidase is particularly preferable among them.

Since commercially available coloring reagents for using in conventional ELISA, for example commercially available benzidine-base coloring reagents for use in ELISA, are hardly soluble in water, they are dissolved in an aqueous solution containing an organic solvent, for example methyl alcohol, 1-methyl-2-pyrrolidone or dimethylsulfoxide. However, the kinds and proportions of the substrate, the proportion of the organic solvent, and pH are adjusted in the invention so that the enzyme reaction product is precipitated on the surface of the optical waveguide.

The coloring reagent solution is prepared as follows.

When the benzidine-base coloring reagent is used as the coloring substrate and hydrogen peroxide is used as the substrate of the labeling enzyme, the concentrations of the benzidine-base coloring reagent and hydrogen peroxide in the coloring reagent solution may be appropriately determined depending on the measuring method and reaction conditions of color development. The content of the benzidine-base reagent in the coloring reagent solution is usually 0.1 to 10 mmol/L, preferably 0.5 to 5 mmol/L, while the content of hydrogen peroxide in the coloring reagent solution is usually 0.1 to 10 mmol/L, preferably 0.5 to 5 mmol/L.

The pH of the buffer solution as a solvent of the coloring reagent is not particularly restricted so long as it is in the range of 3.5 to 7.0, preferably 4.5 to 6.0. For example, known buffer solutions such as an acetate buffer solution, a phosphate buffer solution, a glycine buffer solution, a tris buffer solution and various Good's buffer solutions may be used. Particular examples of the buffer solution include potassium hydrogen phthalate/sodium hydroxide buffer solution, disodium citrate/hydrochloric acid buffer solution, potassium dihydrogen citrate/sodium hydroxide buffer solution, succinic acid/sodium tetraborate buffer solution, potassium hydrogen citrate/sodium tetraborate buffer solution, sodium dihydrogen phosphate/citric acid buffer solution, sodium acetate/hydrochloric acid buffer solution and acetic acid/sodium acetate buffer solution. The preferable concentration of the buffer solution in the coloring reagent solution is 0.1 to 100 mmol/L, particularly 1 to 50 mmol/L.

For preparing the coloring reagent solution, the benzidine-base coloring reagent (coloring substrate) may be directly added to an aqueous medium such as a buffer solution, or a solution in which the benzidine-base coloring reagent is dissolved in a high concentration in another solvent may be added. While the coloring reagent solution of the invention is obtained by adding a peroxide (a substrate of the labeled enzyme) to the solution above, the method for preparing the coloring reagent solution is not particularly restricted thereto.

A component for aiding and stabilizing color development, for example a chelating agent or tripolyphospate, may be added to the coloring reagent solution, if necessary.

The surfactant available is not particularly restricted, and any of cationic, anionic, nonionic and amphoteric surfactants may be employed. The nonionic surfactant is preferable among them for maintaining the activity of the enzyme.

Examples of the nonionic surfactant include those of polyhydroxyl alcohol and polyethyleneglycol types. Examples of the nonionic surfactant of the polyhydroxyl alcohol type include fatty acid esters of glycerin, fatty acid esters of sorbitan, fatty acid esters of pentaerythritol and fatty acid esters of sucrose. While ethyleneoxide is added to the nonionic surfactant of the polyethyleneglycol type, propyleneoxide may be added in a range that maintains solubility in water.

Fatty acid esters of sorbitan are particularly preferable among them. The fatty acids used for the sorbitan fatty acid esters include lauric acid, palmitic acid, stearic acid and oleic acid. Sorbitan fatty acid esters commercially available under the trade names of Tween 20, Tween 40, Tween 60 and Tween 80 from Atlas Powder Co. (USA) may be used as the sorbitan fatty acid esters. Other products are also commercially available under the trade names of Tergito 17, Irgasan and Monesin. These surfactants are added to the coloring reagent solution usually in the range of 0.01 to 50 mg/mL, preferably in the range of 0.5 to 10 mg/mL.

Other coloring reagents that are commercially available for other uses and could not be used for conventional ELISA may be used as the coloring reagent of the invention. For example, coloring reagents commercially available for other immunochemical measuring methods such as western blotting methods, for example BM Blue POD Substrate Precipitating 1-442-066 from Roche Diagnostic GmbH and TMBM Peroxidase Substrate from MOSS, Inc., as coloring reagents for immobilizing on a membrane may be used for the enzyme immunoassay method.

(Sensor Chip)

The sensor chip of the invention comprises an optical waveguide layer capable of propagating a light into the layer by total reflection, and an antibody immobilized layer formed on at least a part of the surface of the optical waveguide layer for allowing the light to totally reflect. The preferable sensor chip comprises a liquid-repelling film formed on the surface of the optical waveguide layer, the film has a surface at a level higher than the antibody immobilized layer, and having a reaction hole exposing at least one part of the antibody immobilized layer. The preferable sensor chip also comprises a frame member for constituting a cell adhered to the surface of the optical waveguide layer, the frame member has a top end elevated from the liquid-repelling film and surrounding the reaction hole.

The sensor chip preferably comprises a cell wall for forming a cell by surrounding the antibody immobilized layer, and the reaction hole is formed in the cell. It is possible to analyze a very small quantity of the measuring object in the test sample solution with high sensitivity and high accuracy by using such sensor chip.

Figure 3:
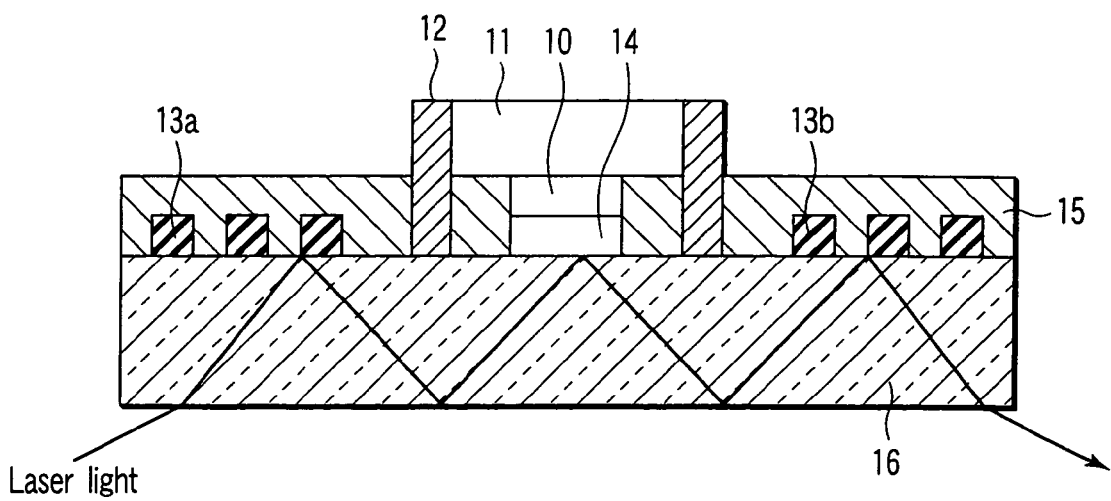
FIG. 3 is a cross section along the line denoted by III in FIG. 2 showing an example of the sensor chip according to the invention.
Figure 4:
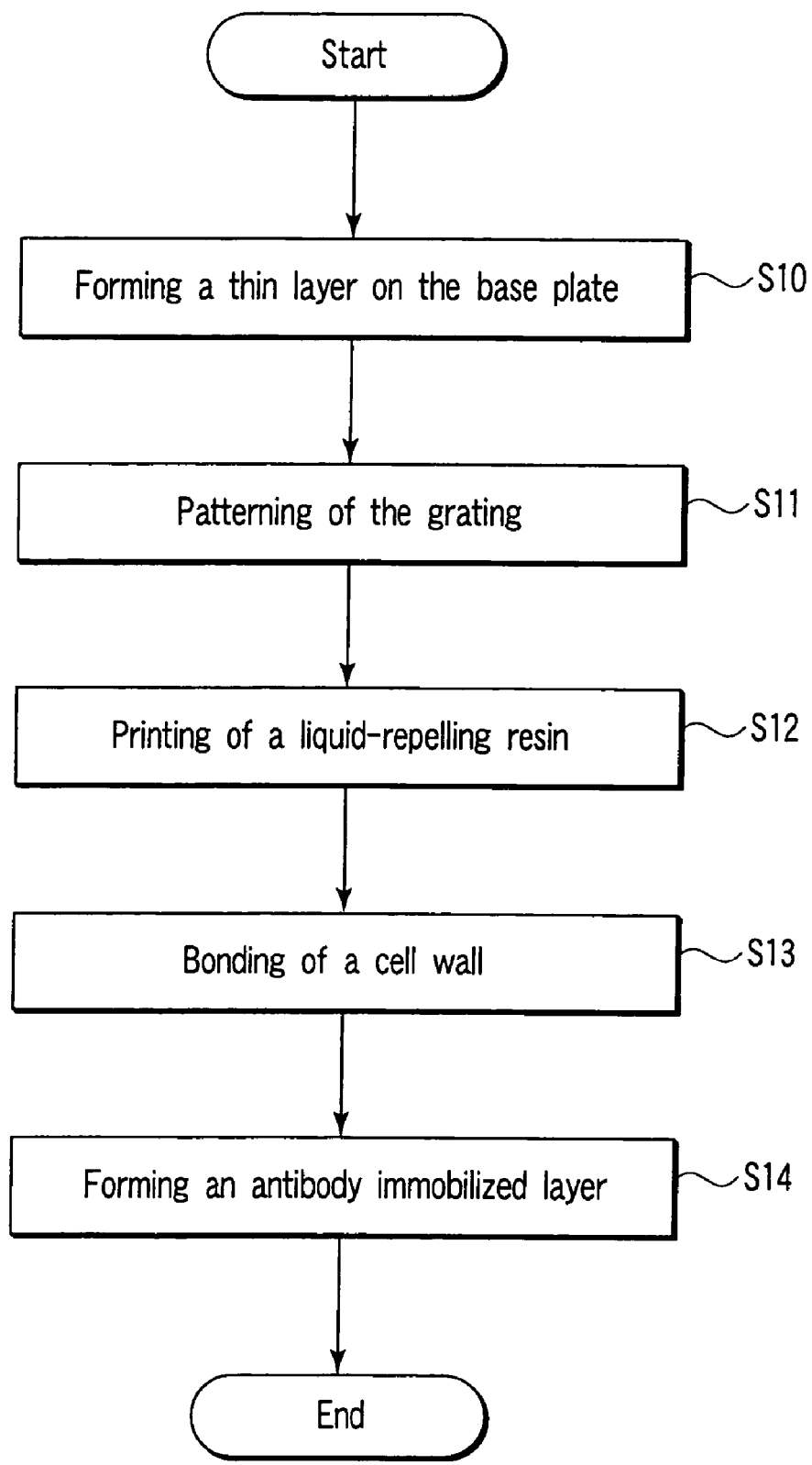
FIG. 4 is a flow chart showing a process for manufacturing the sensor chip according to the embodiment of the invention.

The sensor chip according to an embodiment of the invention is shown in FIGS. 2 and 3. The sensor chip shown in FIGS. 2 and 3 comprises a base plate 16 made of a borosilicate glass, an incident side grating 13a and outgoing side grating 13b located on the surfaces of both sides of the base plate 16, respectively, and an antibody immobilized layer 14 disposed therebetween. The sensor chip also comprises a cell wall 12 surrounding the antibody immobilized layer 14 to form a cell 11. A solvent-repelling resin film 15 having a reaction hole 10 is provided on the bottom surface of the cell 11, except on the upper surfaces of the incident side grating 13a, outgoing side grating 13b and the antibody immobilized layer 14. Such sensor chip is used in combination with a laser oscillator and a photoelectric conversion element for receiving a reflection light.

The thickness of the antibody immobilized layer 14 (the distance from the surface of the optical waveguide to the antibody surface of the antibody immobilized layer) is preferably 30 to 500 nm, more preferably 100 nm or less, and particularly 80 nm or less.

While the enzyme reaction is performed in the reaction hole 10 to form an enzyme reaction product that develops a color and precipitates in the sensor chip of the invention, a volume of the test sample solution of as small as about 1 µL is sufficient for the measurement.

Each device can be prevented from being corroded by manipulation of reagents on the apparatus by providing the cell wall 12. The size and height, the shape of the opening of the frame member and the material of the frame member may be freely determined depending on the convenience of uses, so long as the cell wall 12 is constructed not to reactive to the reagents contained in the measuring kit.

The cell wall forming the frame member is preferably made of a colored resin such as a black resin. The material of the colored resin is not particularly restricted so long as it is not reactive and compatible to the reagents and solvents and has good moldability. An acrylic resin and ABS resin may be selected and used depending on the constitution of the kit.

The frame member constituting the cell wall 12 is directly bonded, with a UV curable adhesive, to the surface of the principal face constituting the total reflection face of the base plate 16 that forms the optical waveguide layer, so as to block one end of the opening. The cell wall 12 is provided in order to surround a measuring area, so that reagent solutions such as the reagent and test sample solutions and cleaning liquid injected into the reaction hole 10 do not leak to the outside. Accordingly, the height (thickness) from the surface of the base plate defined by the top end of the frame member is adjusted to be higher than the height of the liquid-repelling resin film 15.

The liquid-repelling resin film 15 is provided so that it covers at least a part of the antibody immobilized layer 14 among the surface of the principal face constituting the total reflection face of the base plate 16 and throughout the remaining portion except the region where the cell wall 12 is provided. A light-shielding colored resin such as a black resin is preferably used for the liquid-repelling resin 15 so that the light impinging from the downward of the base plate 16 do not leak to the outside. While the liquid-repelling resin is not particularly restricted so long as it is not reactive and compatible to the solvents in the kit and has a good solvent-repelling or water-repelling property, a fluorinated resin is preferable.

The incident side grating 13a and outgoing side grating 13b are preferably formed of titanium oxide ($TiO_2$), tin oxide ($SnO_2$), zinc oxide, lithium niobate, gallium arsenide (GaAS), indium-tin oxide (ITO) and polyimide.

While the gratings 13a and 13b has an optical function for introducing and irradiating a laser light to the sensor chip, this function is not always necessary provided that the same function can be obtained using other members. Other optical elements such as a prism may be provided so long as it can realize the same function.

The antibody immobilized layer 14 has, for example, a structure in which an antibody is immobilized with a cross-linking polymer. Examples of the cross-linking polymer used in the antibody immobilized layer 14 include a polymer having hydrogen bonding functional groups such as photocross-linking polyvinyl alcohol. Since the antibody is usually hydrophilic, the antibody immobilized layer is also preferably hydrophilic.

(Method for Manufacturing Sensor Chip)

The process for manufacturing the sensor chip is described with reference to FIGS. 4, 5A to 5E, and 6.

Figure 5A:
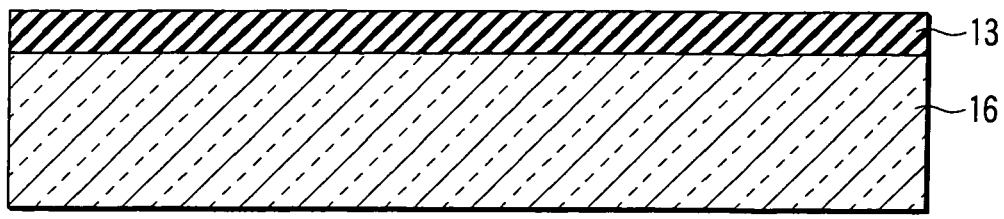
FIGS. 5A, 5B, 5C, 5D and 5E show a step in the process for manufacturing the sensor chip according to the embodiment of the invention.

S10: As shown in FIG. 5A, a thin film is formed by depositing, for example, titanium oxide on the surface of a base plate 16 made of a borosilicate glass by sputtering or spin coating.

Figure 5B:
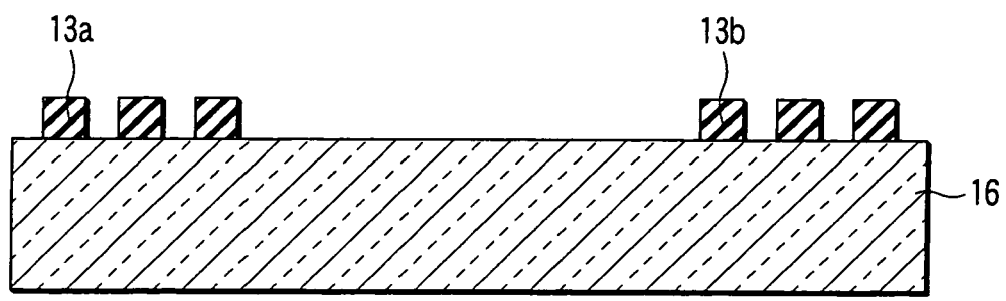

S11: Subsequently, an incident side grating 13a and outgoing side grating 13b are patterned on the surface of both sides of the base plate by selectively etching the thin film by photo-etching as shown in FIG. 5B. An optical waveguide layer with a thickness of 1 µm having gratings is formed by this step.

Figure 5C:
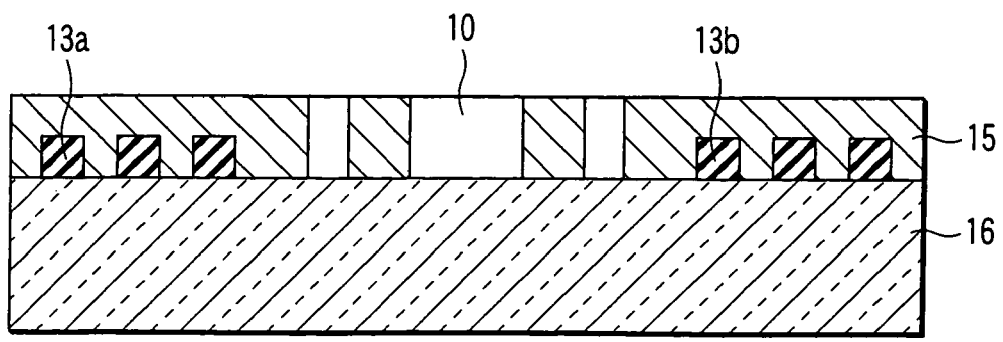

S12: Then, as shown in FIG. 5C, a liquid-repelling resin layer 15, for example a layer of a light-shielding colored fluorinated resin, is printed on the portion of the surface of the base plate 16 except the portions of a reaction hole 10 and cell wall 12 to form a fluorinated resin film.

Figure 5D:
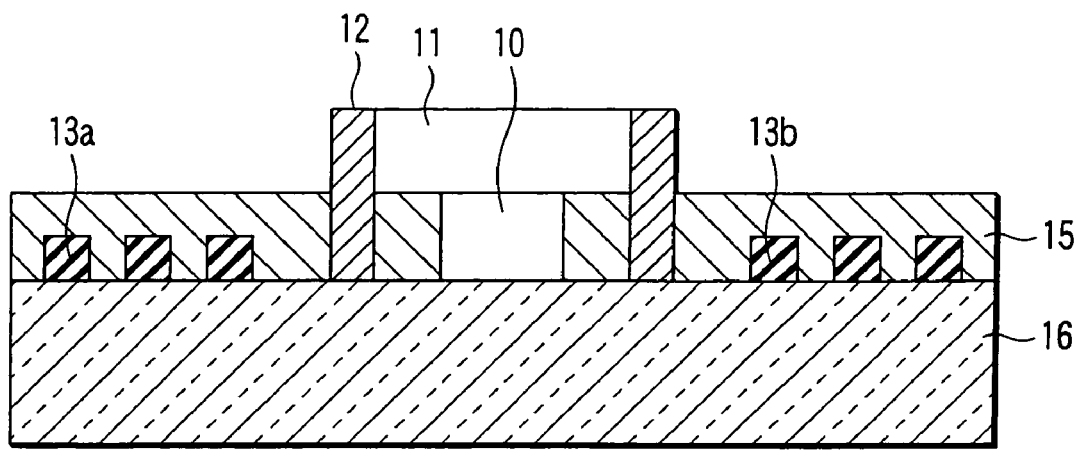

S13: Then, as shown in FIG. 5D, a cell wall 12 made of a black acrylic resin is provided so as to surround the reaction hole 10. The cell wall is bonded to the base plate 16 using a UV-curable adhesive to form a cell 11.

Figure 5E:
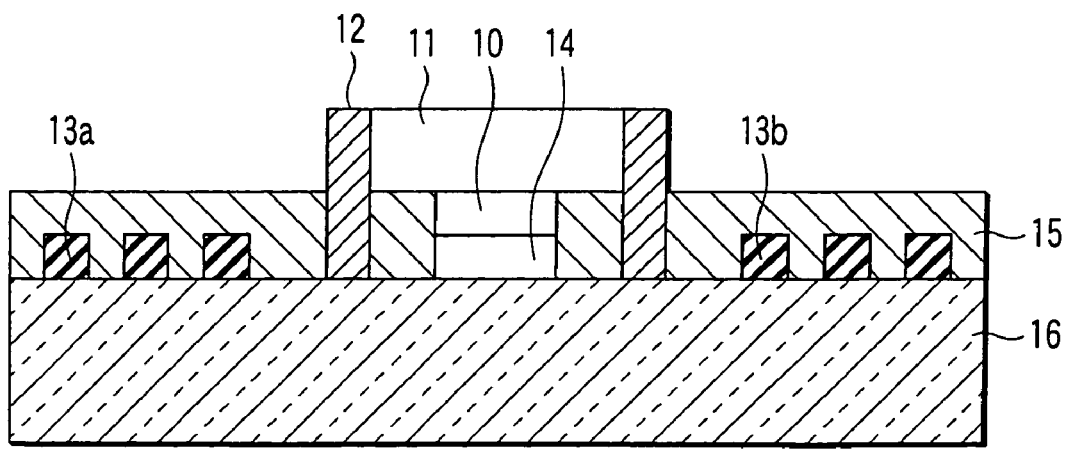
Figure 6:
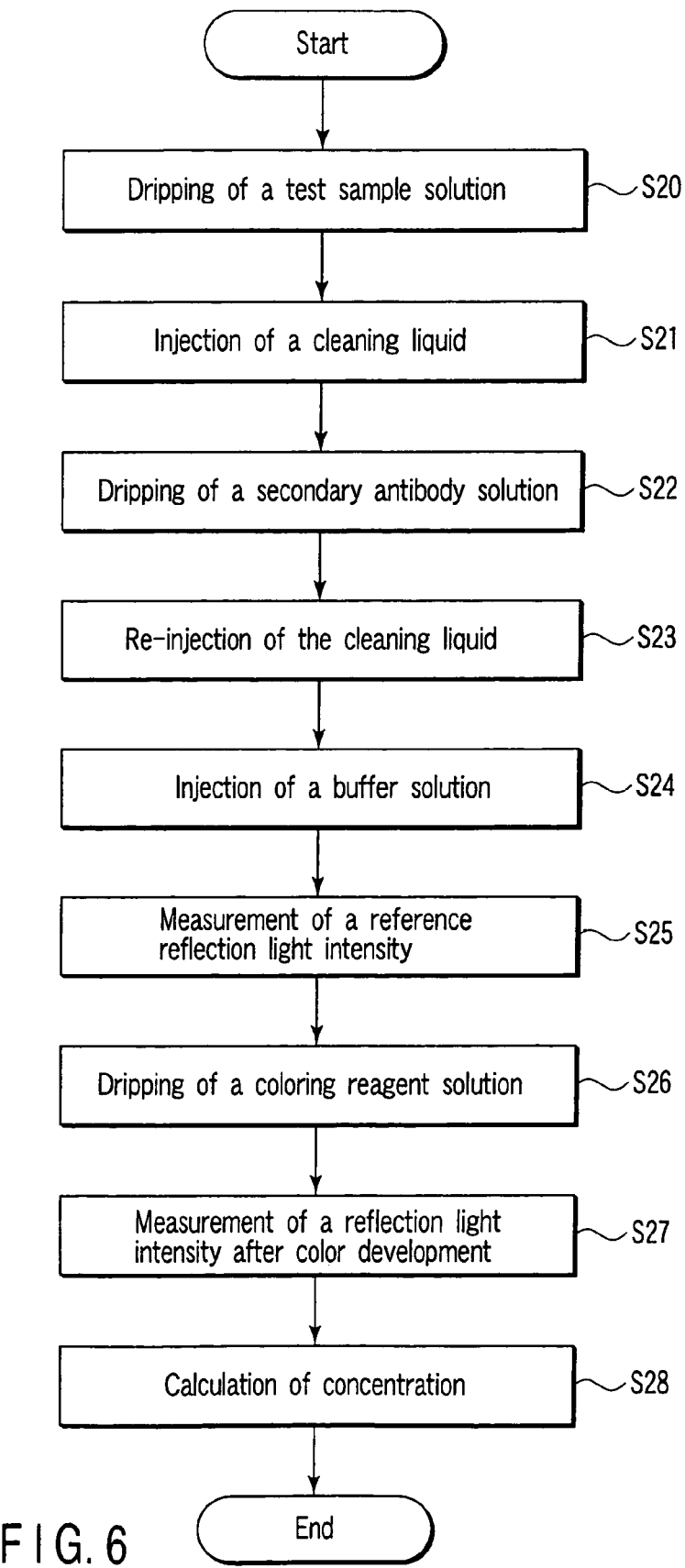
FIG. 6 is a flow chart showing a process of the measuring method using the sensor chip according to the embodiment of the invention.

S14: Subsequently, an antibody immobilized layer 14 is formed in the reaction hole 10 as shown in FIG. 5E. Specifically, (1) the surface of the base plate 16 is modified with amino groups by silane coupling treatment using aminosilane as a silane coupling agent; (2) the surface of the base plate is then treated with glutaraldehyde to immobilize the antibody on the base plate 16 by cross-linking; and (3) excess amino groups are finally blocked with bovine serum albumin (BSA) to form the antibody immobilized layer 14.

(Method for Measuring the Concentration of Measuring Object)

The method for measuring the concentration of the measuring object uses the sensor chip having the optical waveguide and the antibody immobilized layer formed on the surface of the optical waveguide layer, comprises: immobilizing a test sample on the antibody immobilized layer of the sensor chip by dripping a test sample solution and an enzyme-labeled antibody solution on the antibody immobilized layer and allowing an antigen-antibody reaction; dripping a coloring reagent solution on the antibody immobilized layer to precipitate an enzyme reaction product in the antibody-immobilized layer; allowing to totally reflecting a light impinged on the sensor chip from the outside at an interface between the optical waveguide layer and the antibody immobilized layer; and observing to a physical value of the totally reflected light.

In other words, the method for measuring the concentration according to the invention comprises the steps of: providing the antibody immobilized layer on which a first antibody is immobilized on the surface of the optical waveguide layer made of a light-transmitting base plate; immobilizing the measuring object using the antibody immobilized layer; allowing an enzyme-labeled secondary antibody to react with the measuring object; and obtaining the enzyme reaction product by adding a coloring reagent that changes the amount of the reaction depending on the amount of the immobilized measuring object. An evanescent wave of the total reflection light propagating in the optical waveguide layer is subjected to a change of the physical value, for example decay of the light intensity, corresponding to the amount of the enzyme reaction product, when the light is totally reflected in the region where the enzyme reaction product exists. The measurement of the concentration of the measuring object (test sample) is possible by observing the change of the physical value of the light between in the presence and absence of the enzyme reaction product.

When a conventional coloring reagent solution comprising a substrate of a labeled enzyme and a coloring substrate is used, the pigment after color development is diffused into the entire coloring solution since the pigment after color development is soluble. In this case, absorption and scattering by the pigment cannot be substantially detected using the evanescent wave that reaches to a depth of only about 2 μm from the surface of the base plate.

Accordingly, a coloring reagent solution in which the enzyme reaction product precipitates after the enzyme reaction is used in the method of the invention. Since the enzyme reaction product is precipitated on the antibody immobilized layer, and the evanescent wave is allowed to totally reflect at the antibody immobilized layer, the distance (the thickness of the antibody immobilized layer) from the surface of the optical waveguide layer to the surface of the antibody immobilized layer is preferably adjusted to 30 to 500 nm, more preferably to 100 nm or less, and particularly to 80 nm or less.

The temperature for the enzyme reaction is preferably an optimum temperature for the reaction of the enzyme used for labeling the antibody. The temperature is usually 20 to 50° C. when an enzyme such as peroxidase is used.

The quantity of the test sample for use in the measurement may be a given amount or more for detecting information in the vicinity of the optical waveguide layer by taking advantage of the evanescent wave after the primary reaction, secondary reaction and enzyme reaction on the surface of the light permeable base plate. The concentration of the measuring object such as insulin may be determined even when the amount of the test sample for use in the measurement is inaccurate.

Not only the intensity of the transmitted light is measured as in the conventional method using a microplate, but also the change of the physical value of the reflection light by absorption of the evanescent wave caused by total reflection at the antibody immobilized layer is observed in the method of the invention. Accordingly, a small surface area is required for the measurement, which is possible by using 0.5 μL or less of the test sample, usually by using 1.0 to 5 μL of the test sample, and by using 1.0 to 2 μL of the test sample under a suitable condition.

The reaction time is shortened when the amount of the test sample for use in the measurement is small. The primary reaction is completed within 1 hour, or within 20 minutes under a suitable condition, or within 10 minutes under an optimum condition, and the secondary reaction and enzyme reaction are completed within 20 minutes, or in about 10 minutes under a suitable condition. Therefore, it is possible to reduce the entire measuring time for measuring the concentration of the measuring object to within 1 hour, or to within 20 minutes under a suitable condition.

In the measurement of the physical value of the totally reflected light, it is sufficient to detect only the change of the physical value of the totally reflected light. Accordingly, not only the zero order light of the totally reflected light but also diffracted light, or higher order of the totally reflected light such as primary and secondary orders of light may be observed using an appropriate phenomenon or method.

(Method for Measuring Insulin)

The rat insulin concentration is measured by the following method.

First, the sensor chips are aligned on a plate for temporarily placing the chips, 1 μL each of the test sample solution is dripped at the center of the cell (cell 11 in FIGS. 2 and 3) of the sensor chip, and the sample is allowed to react (primary reaction) at room temperature for 10 minutes while the test sample solution is kept at the center of the cell.

Then, the cell of each sensor chip is washed using 8-conneted pipette.

Subsequently, 20 μL each of a solution prepared by mixing an enzyme-labeled guinea pig anti-rat insulin solution and a dilution solution of the enzyme-labeled guinea pig anti-rat insulin is dripped into each cell, and the sample is allowed to react (secondary reaction) at room temperature for 10 minutes.

After washing the cell of each chip, 25 μL of a phosphate buffer solution is dripped into the cell of each chip.

Subsequently, the chip after the secondary reaction is set in a concentration measuring apparatus using a concentration measuring apparatus for immunoassay by the optical waveguide to determine an initial value obtained by adding the phosphate buffer solution in each cell.

The phosphate buffer solution is removed, and 20 μL each of a coloring reagent solution containing a coloring substrate and a substrate for the labeling enzyme is dripped into each cell to allow the enzyme reaction to advance. A laser light is irradiated to the sensor chip thereafter using a concentration measuring apparatus, and the physical value of the laser light after absorbing the energy through the antibody immobilized layer is measured by receiving the light with a silicon photodiode of the concentration measuring apparatus. The measurement may be repeated plural times with a lapse of time to obtain time-dependent changes.

The mechanism of the measuring method by sandwich ELISA using the sensor chip will be described in more detail below using FIGS. 6 and 7A to 7D.

Figure 7A:
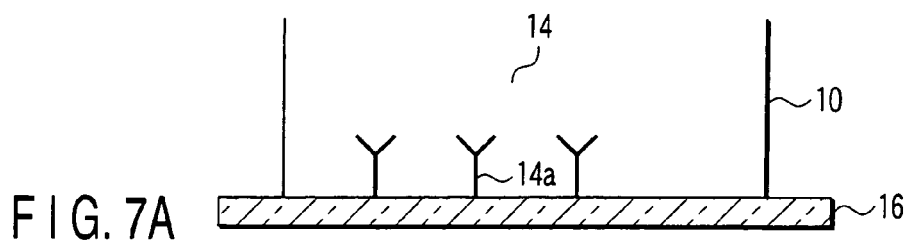
FIGS. 7A, 7B, 7C and 7D describe a step in the process of the measuring method using the sensor chip according to the embodiment of the invention.
Figure 7B:
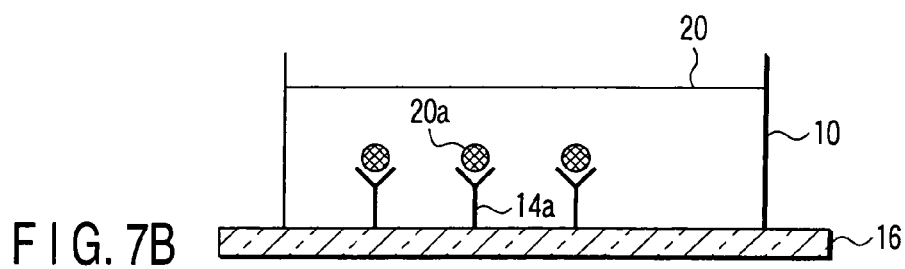

S20: The antibody immobilized layer 14 comprising a primary antibody 14a for specifically recognizing an antigen 20a as a measuring object such as a protein or gene is formed on the surface of the base plate 16 of the reaction hole 10 of the sensor chip as shown in FIG. 7A. A test sample solution 20 (1.0 to 5 μL) containing the antigen 20a is dripped on the antibody immobilized layer 14 in the reaction hole 10. Then, as shown in FIG. 7B, the antigen 20a binds to the primary antibody 14a to form a primary antibody/antigen complex.

S21: Then, the test sample solution 20 excluding the antigen 20a immobilized on the primary antibody 14a is washed away with a phosphate buffered physiological saline (PBS) containing a surfactant for enhancing cleaning efficiency.

S22: A solution 21 of a secondary antibody labeled with an enzyme is then dripped. The solution of the enzyme-labeled secondary antibody available is a secondary antibody labeled with horseradish peroxidase contained in a Tris-HCl buffer solution (pH 6.0 to 9.0, preferably 7.0 to 8.0) having a composition comprising 0.1 to 5% by volume, preferably 0.3 to 1.5% by volume of insulin-free rat serum, 0.01 to 1% by volume, preferably 0.05 to 0.1% by volume of Tween 20 (manufactured by Atlas Powder Co.), and 0.1 to 1 mol, preferably 0.1 to 0.2 mol of NaCl.

Figure 7C:
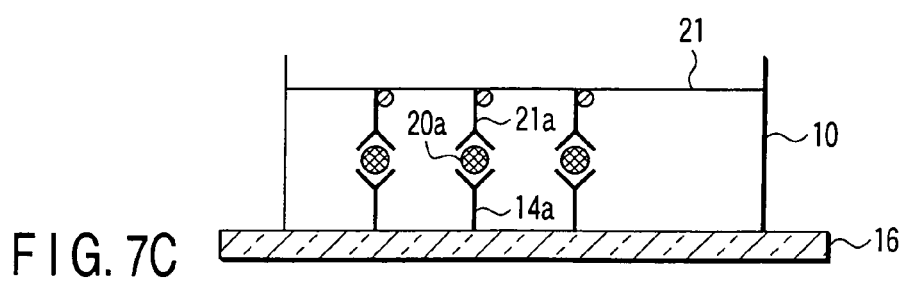

When the solution 21 of the enzyme-labeled secondary antibody is dripped, the secondary antibody 21a additionally binds to the antigen 20a at a different site from that of the primary antibody 14a as shown in FIG. 7C. As a result, an immune complex composed of primary antibody/antigen/secondary antibody is formed. A redox enzyme such as peroxidase may be used as the labeling enzyme labeled on the secondary antibody 21a.

S23: subsequently, the secondary antibody solution 21 containing the secondary antibody 21a that did not form the immune complex is washed again using a cleaning solution such as a phosphate buffer solution containing a surfactant.

S24: Then, the surfactant used for washing is removed, and only the phosphate buffer solution is injected for stabilizing the immune complex.

S25: A laser light is irradiated to the incident side grating 13a of the sensor chip, and the laser light is propagated into the optical waveguide layer to generate an evanescent wave from the surface of the optical waveguide layer. The propagated light is received with a photo-acceptance element as a reflection light from the outgoing side grating 13b, and the intensity of the light is measured as a reference reflection light intensity.

Figure 7D:
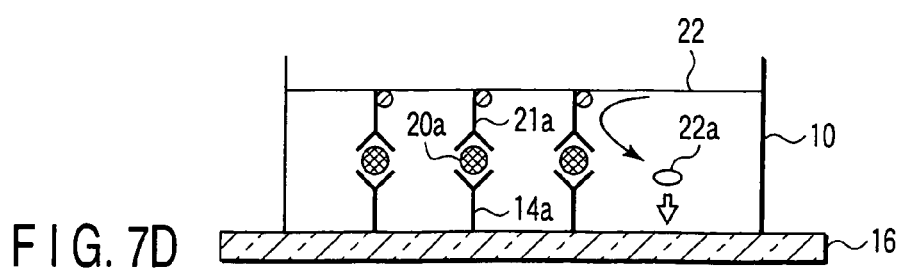

S26: Subsequently, the phosphate buffer solution injected in S24 is removed, and a coloring reagent solution 22 is dripped in the cell 11 as shown in FIG. 7D. The preferably used coloring reagent solution 22 contains acetic acid, TMBZ, hydrogen peroxide ($H_2O_2$) and a small amount of an organic solvent such as dimethylsulfoxide. A radical oxygen atom (O*) is formed by a redox enzyme reaction of a labeling enzyme such as peroxidase (POD) and $H_2O_2$ as a substrate of the labeling enzyme (POD). The coloring reagent 22a is oxidized with the radical oxygen atom (O*) formed by the enzyme reaction, and the —$NH_2$ group of TMBZ is oxidized to =NH group to develop a bluish-green color. The oxidized coloring reagent is insolubilized and precipitates on the antibody immobilized layer 14 (the surface of the base plate 16).

S27: Subsequently, a laser light is irradiated to the sensor chip as in the measurement of the reference reflection light intensity. When the laser light is irradiated from a light emitting element to the incident side grating 13a of the sensor chip, the incident laser light propagate into the base plate 16 as the optical waveguide layer by total reflection through the incident side grating 13a. The evanescent wave is generated on the surface of the optical waveguide layer when the laser light is totally reflected. The evanescent wave is absorbed by the precipitated enzyme reaction product. This action gives a slight change to the propagating light. The reflection light from the outgoing side grating 13b is sensed by the light-receiving element, and the reflection light intensity after the color development is measured.

S28: A difference between the reference reflection light intensity measured in S25 and the reflection light intensity after the color development in S27 is determined, and the concentration of the antigen 20a as the measuring object in the test sample solution 20 is calculated to determine the concentration of the measuring object in the test sample solution.

According to the method of the invention, the coloring reagent solution 22 develops a color while the coloring reagent 22a is precipitated on the antibody immobilized layer 14 as an enzyme reaction product by the enzyme reaction on the antibody immobilized layer 14. Consequently, the evanescent wave generated on the surface of the base plate 16 can be reliably absorbed at the interface between the optical waveguide layer and antibody immobilized layer. Therefore, since a very fine change of the light propagating through the optical waveguide layer can be detected even when the amount of the sample in the sample solution is very small, a highly sensitive measurement, analysis and quantification is possible.

A graph as shown in FIG. 8 is obtained by continuously measuring the reflection light intensity using the measuring method of the invention. The reference reflection light intensity is determined as the value at A point, and the reflection light intensity after the color development is determined as the value at B point, and then the concentration can be calculated. Therefore, measurements of the reference reflection intensity by reference experiments using a solution containing no antigen is not required.

According to the measuring method of the invention, the change of the physical value of the reflection light of the evanescent wave is measured when the light is totally reflected at a precipitate area of the antibody immobilized layer, instead of measuring the reflection light intensity in the well of the micro-plate as in the conventional method. Accordingly, the concentration of the measuring object can be promptly measured with a high sensitivity and high accuracy using a test sample with a volume of as small as 5 μL or less. In addition, correlation between the method of the invention and conventional ELISA is good even when the amount of the test sample for use in the measurement is distributed in the range of 1.0 to 5 μL, and the concentration of the measuring object can be obtained with excellent reproducibility.

Since the amount of the test sample is small, the measuring time is shortened. The total measuring time is within 1 hour, or within 20 minutes under a suitable condition.

Selectively precipitating the pigment permits selective detection of the pigment. Since the measurement is hardly affected by non-selectively adsorbed proteins, a sample containing multiple components such as blood may be stably measured.

While the method of the invention is applicable to sandwich ELISA, it can be applied to ELISA other than sandwich ELISA.

While the method of the invention is described in more detail hereinafter with reference to examples, the method is by no means restricted to these examples.

EXAMPLE 1

The concentration was measured using the sensor chip shown in FIG. 1. An anti-insulin antibody was immobilized on an antibody immobilized layer 14 (in a circle with a diameter of 2 mm) in reaction holes 10 on a transparent glass base plate.

A rat insulin solution (10 ng/mL) as a test sample was dripped onto the antibody immobilized layer 14 by changing the volume in the range of 0.5 to 2 μL. After a primary reaction for 10 minutes at room temperature, the surface of the glass base plate was washed with a phosphate-buffered physiological saline (containing 1% of a nonionic surfactant (Tween 20; manufactured by Atlas Powder Co.)). A secondary antibody solution (20 mmol of Tris-HCl buffer solution containing 1% by volume of insulin-free rat serum, 0.05% by volume of Tween 20 manufactured by Atlas Powder Co., and 0.15 mol of NaCl, pH7.4) labeled with horseradish peroxidase was dripped, and the sample was subjected to a secondary reaction for 10 minutes at room temperature. After the secondary reaction, the reaction system was washed with the buffer solution described above followed by washing with a phosphate buffer solution at pH6.0 to measure a reference reflection light intensity as a reference value. After the measurement, a coloring reagent solution (tetramethyl benzidine 1.1 mmol/L, Hydrogen peroxide 1.9 mmol/L, dimethylsulfoxide 1% by volume, acetate buffer solution 80 mmol/L, pH4.9) was dripped, and the solution was allowed to stand for 10 minutes.

Subsequently, a measuring laser light was introduced the glass base plate through an incident side grating, and was allowed to totally reflect on the back face of the circular area (sensing area) of the antibody immobilized layer. Since the reflection light is radiated out of the glass base plate by the outgoing side grating, the intensity of radiation was measured with a light-reception element (a photo-diode). The intensity of the light flux changes after total reflection in response to absorption and reflection of the evanescent wave impinging into the sensing area during total reflection. Accordingly, the ratio between the reflection light intensity before the enzyme reaction and the reflection light intensity after the enzyme reaction (referred to reduction ratio hereinafter) is correlated with the concentration of the measuring object (insulin).

The results of measurements obtained by changing the amount of the test sample are shown in FIG. 9. The quantity of the test sample was plotted along the horizontal axis, and the reduction ratio was plotted along the vertical axis. The reduction ratio is approximately constant at the quantity of the test sample of 1 µL or more, which shows that the insulin concentration can be measured even when the quantity of the test sample for use in the measurement is not accurate, or the result is independent of the quantity of the test sample.

The results of measurements when the concentration of the test sample is changed are shown in FIG. 10. When the insulin concentration is plotted along the horizontal axis and the reduction ratio is plotted along the vertical axis, an approximately linear calibration curve was obtained with a correlation coefficient ($R^2$) of 0.998. The calibration curve is represented by a linear function approximated by y 3.8902x+1.5581 (where x represents the insulin concentration and y represents the reduction ratio).

EXAMPLE 2

Figure 11:
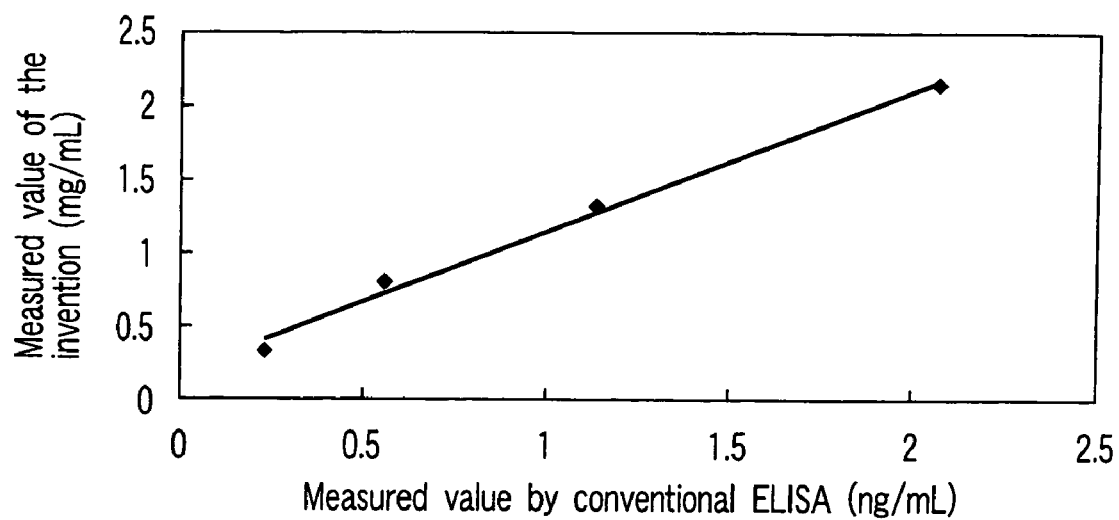
FIG. 11 shows correlation (a calibration curve) between the measured value using the sensor chip and the measured value using a conventional microplate obtained in Example 2 (rat whole blood).

The insulin concentration was measured using the whole blood of rat as a test sample by the same method as in Example 1. Correlation between this result and the result of conventional ELISA was investigated. The results are shown in FIG. 11. As shown in FIG. 11, a good linear calibration curve was obtained with a correlation coefficient ($R^2$) of 0.9919. The calibration curve is represented by a linear function approximated by y=0.9658x+0.1759 (where x represents the measured value by conventional ELISA and y represents the measured value by the method of the invention).

Conventional ELISA was measured as follows.

After dispensing 95 µL of a buffer solution containing insulin-free rat serum into an antibody immobilized microplate, 5 µL of rat whole serum or 5 µL of diluted solutions of reference insulin with an insulin concentration of 0 to 5000 µg/mL were dispensed, and the samples were allowed to react at room temperature for 1 hour. Then, after washing the wells, a peroxidase-labeled antibody was added to each well, and the sample was allowed to react at room temperature for 1 hour. After washing the well, 100 µL of a coloring reagent solution ($H_2O_2$, TMBZ solution) was added, and the sample was allowed to react at room temperature for 40 minutes by shielding light. After stopping the enzyme reaction by adding 50 µL of an enzyme reaction stop solution, absorbance of the well was measured at a principal wavelength of 450 nm and a sub-wavelength of 630 nm using a microplate reader.

EXAMPLE 3

Figure 12:
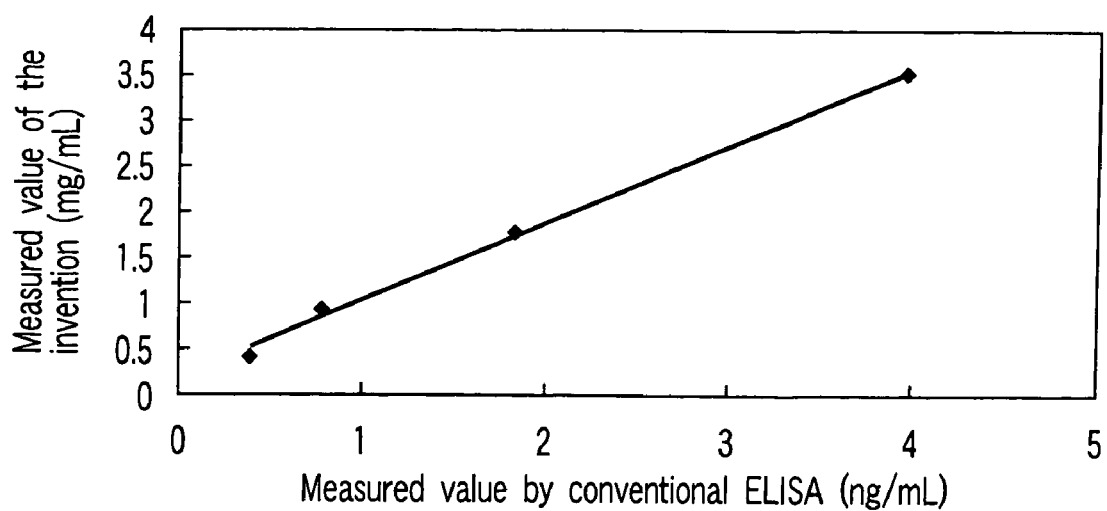
FIG. 12 shows correlation (a calibration curve) between the measured value using the sensor chip and the measured value using a conventional microplate obtained in Example 3 (rat plasma).

The insulin concentration was measured using rat plasma as a test sample by the same method as in Example 1. Correlation between this result and the result by conventional ELISA described in Example 2 was investigated. The results are shown in FIG. 12. As shown in FIG. 12, a calibration curve showing good linearity with a good correlation coefficient ($R^2$) of 0.9969 was obtained. This calibration curve can be approximated by a linear function of y=0.8508x+0.195 (where x is the measured value by conventional ELISA and y is the measured value by the method of the invention).

EXAMPLE 4

The change of the reflection light intensity was measured by the same method as in Example 1 using 2 µL of a casein antigen solution with a concentration of 50 ng/mL as a test sample, an anti-casein antibody as a primary antibody, and an enzyme-labeled anti-casein antibody as a secondary antibody.

The reflection light is radiated out of the glass base plate by the outgoing side grating; the intensity thereof is measured with a photo-reception element (photodiode); and a sensor output with a significant intensity relative to a blank value (45.0%) was obtained. The results are shown in FIG. 13.

EXAMPLE 5

The change of the reflection light intensity was measured by the same method as in Example 1, except that β-lactoglobulin was used in place of casein in Example 4, and an anti-β-lactoglobulin antibody as a primary antibody and an enzyme-labeled anti-β-lactoglobulin antibody as a secondary antibody were used. The sensor output relative to the blank value was 11.70%. The results are shown in FIG. 14.

EXAMPLE 6

The change of the reflection light intensity was measured by the same method as in Example 1, except that ovoalbumin was used in place of casein in Example 4, and an anti-ovoalbumin antibody as a primary antibody and an enzyme-labeled anti-ovoalbumin antibody as a secondary antibody were used. The sensor output relative to the blank value was 34.6%. The results are shown in FIG. 15.

EXAMPLE 7

The change of the reflection light intensity was measured by the same method as in Example 1, except that a major protein complex of buckwheat was used in place of casein in Example 4, and an anti-buckwheat major protein complex antibody as a primary antibody and an enzyme-labeled anti-buckwheat major protein complex antibody as a secondary antibody were used. The sensor output relative to the blank value was 30.8%. The results are shown in FIG. 16.

EXAMPLE 8

Figure 17:
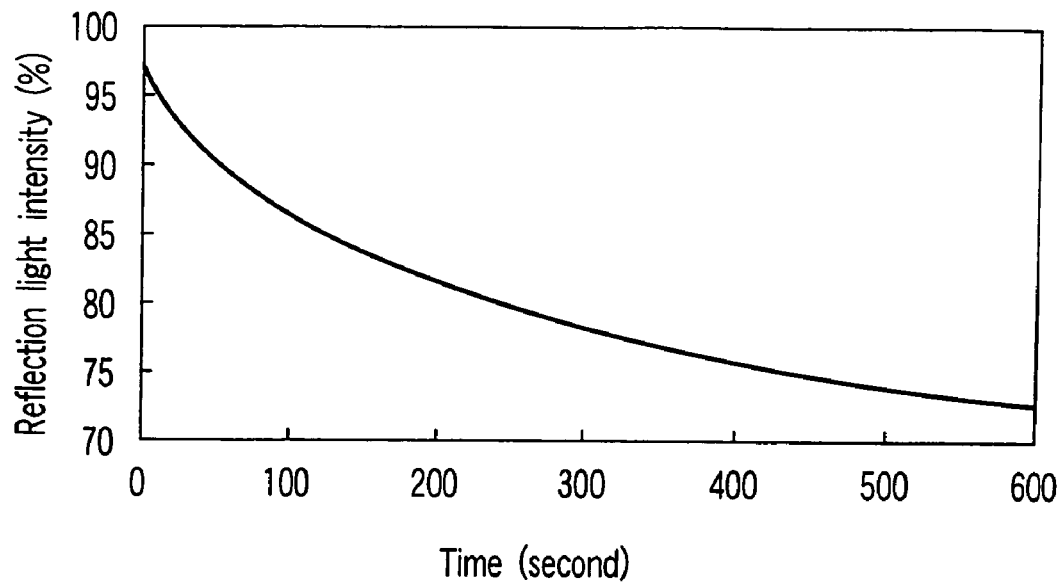
FIG. 17 is a graph showing the result of measurement on a soluble protein containing Arah2 of peanuts obtained in Example 8.

The change of the reflection light intensity was measured by the same method as in Example 1, except that a soluble protein containing Arah2 of peanuts was used in place of casein in Example 4, and an anti-peanuts Arah2 soluble protein antibody as a primary antibody and an enzyme-labeled peanuts Arah2 soluble protein antibody as a secondary antibody were used. The sensor output relative to the blank value was 27.4%. The results are shown in FIG. 17.

EXAMPLE 9

The concentration of human insulin was measured in Example 1 using a human insulin solution as a test sample. The results are shown in FIG. 18.

Figure 18:
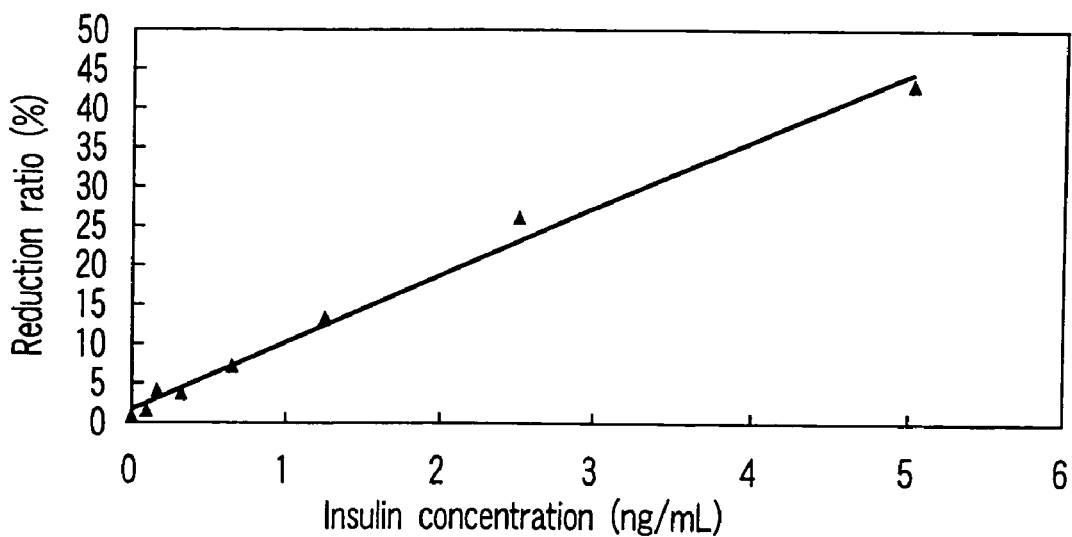
FIG. 18 is a graph showing the result of measurement on human insulin obtained in Example 9.

When the insulin concentration is plotted along the horizontal axis and the reduction ratio is plotted along the vertical axis, a linear calibration curve was obtained with a good correlation coefficient ($R^2$) of 0.9908 as shown in FIG. 18. The calibration curve is represented by a linear function approximated by y=8.6108x+1.5289 (where x represents the insulin concentration and y represents the reduction ratio).

Additional advantages and modifications will readily occur to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents.

What is claimed is:

1. A method for measuring the concentration of an analyte, which comprises:
   (i) obtaining a sensor chip comprising:
      an optical waveguide layer configured to propagate a light within the layer by total reflection of the light,
      an antibody-immobilized layer, having an immobilized antibody, formed on at least a part of a surface of the optical waveguide layer,
      a frame member adhered on a surface of the optical waveguide layer, surrounding the antibody-immobilized layer, for constituting a cell, and
      a liquid-repelling film formed on a part of the optical waveguide layer except where a frame member is located, said film having a surface level higher than the antibody-immobilized layer and lower than the frame member to form a reaction hole that exposes at least one part of the antibody-immobilized layer;
   (ii) immobilizing the analyte and an enzyme-labeled antibody, which is labeled with a labeling enzyme, on the antibody-immobilized layer in the reaction hole of the sensor chip;
   (iii) precipitating a color-developed enzyme reaction product by allowing a coloring reagent and the labeling enzyme on the antibody-immobilized layer to react;
   (iv) reflecting totally a light impinged on the sensor chip from the outside at an interface between the optical waveguide layer and the antibody-immobilized layer;
   (v) detecting a change in reflection light intensity caused absorption of an evanescent wave by the color-developed enzyme reaction product at the antibody-immobilized layer; and
   (vi) measuring a concentration of the analyte based on the change of the reflection light intensity.

2. The method according to claim 1, wherein the antibody-immobilized layer has a thickness of 30 nm to 500 nm.

3. The method according to claim 1, wherein the labeling enzyme is horseradish peroxidase.

4. The method according to claim 1, wherein the coloring reagent is a benzidine-base coloring reagent selected from the group consisting of 4-chloro-1-naphtol, 3,3'-diaminobenzidine and 3,3',5,5'-tetramethyl benzidine.

5. The method according to claim 4, wherein the coloring reagent is 3,3',5,5'-tetramethyl benzidine.

6. The method according to claim 1, wherein the analyte is selected from the group consisting of insulin, casein, β-lactoglobulin, ovoalbumin, calcitonin, C-peptide, leptin, β-2-microgloburin, lethinol-binding protein, α-1-microglobulin, α-fetoprotein, carcinoembryonic antigen, troponin-I, glucagons-like peptide, insulin-like peptide, tumor growth factor, fibroblast growth factor, platelet growth factor, epithelial cell growth factor, cortisol, triiode thyronine, thyroxin, digoxin, theophylline, bacteria, viruses, hepatitis antibody, and IgE, major protein complex of buckwheat, and soluble proteins including Arah2 of peanuts.

7. The method according to claim 6, wherein the analyte is insulin.

8. A kit for measuring the concentration of an analyte, which comprises:
   an antibody labeled with a labeling enzyme;
   a coloring reagent comprising at least a coloring substrate and a substrate for the labeling enzyme, the coloring reagent developing a color by an enzyme reaction and forming a precipitating enzyme reaction product; and
   a sensor chip, comprising:
   an optical waveguide layer configured to propagate a light within the layer by total reflection of the light;
   an antibody-immobilized layer, having an immobilized antibody, formed on at least a part of a surface of the optical waveguide layer;
   a frame member adhered on a surface of the optical waveguide layer, surrounding the antibody-immobilized layer, for constituting a cell; and
   a liquid-repelling film formed on a part of the optical waveguide layer except where a frame member is located, said film having a surface at a level higher than the antibody-immobilized layer and lower than the frame member to form a reaction hole that exposes at least one part of the antibody immobilized layer,
   wherein the sensor chip, the antibody and the coloring reagent are independently packed and assembled together.

9. The kit according to claim 8, wherein the coloring substrate is a benzidine-base coloring reagent and the labeling enzyme is peroxidase.

10. The kit according to claim 8, wherein the antibody is any one of an anti-insulin antibody, an anti-casein antibody, an anti-β-lactoglobulin antibody, an anti-ovoalbumin antibody, an anti-buckwheat major protein complex antibody and an anti-peanuts Arah2 soluble protein.

11. The kit according to claim 10, wherein the antibody is the anti-insulin antibody.

12. The kit according to claim 8, wherein the coloring reagent is a benzidine-base coloring reagent selected from the group consisting of 4-chloro-1-naphtol, 3,3'-diaminobenzidine and 3,3', 5,5'-tetramethyl benzidine.

13. The kit according to claim 12, wherein the coloring reagent is 3,3',5,5'-tetramethyl benzidine.

14. A sensor chip comprising:
   an optical waveguide layer configured to propagate a light within the layer by total reflection of the light;
   an antibody-immobilized layer that forms at least a part of the surface of the optical waveguide layer for total reflection of the light;
   a frame member adhered on the surface of the optical waveguide layer, surrounding the antibody-immobilized layer, for constituting a cell; and
   a liquid-repelling film formed on a part of the optical waveguide layer, except where a frame member is located, said film having a surface at a level higher than the antibody-immobilized layer and lower than the frame member, and having a reaction hole exposing at least one part of the antibody-immobilized layer.

15. The sensor chip according to claim 14, wherein the antibody immobilized layer has a thickness of 30 nm to 500 nm.

16. The sensor chip according to claim 14, wherein the antibody-immobilized layer is hydrophilic.

* * * * *